United States Patent [19]

Sears

[11] E Re. 30,748

[45] Reissued Sep. 22, 1981

[54] PHOSPHATIDYL QUATERNARY AMMONIUM COMPOUNDS

[76] Inventor: Barry D. Sears, 5 Cleveland Rd., Marblehead, Mass. 01945

[21] Appl. No.: 93,631

[22] Filed: Nov. 13, 1979

Related U.S. Patent Documents

Reissue of:

[64] Patent No.: 4,086,257
Issued: Apr. 25, 1978
Appl. No.: 731,132
Filed: Oct. 12, 1976

[51] Int. Cl.[3] ..... A23J 7/00; C07F 9/02

[52] U.S. Cl. ..... 260/403

[58] Field of Search ..... 260/403

[56] References Cited

U.S. PATENT DOCUMENTS 2,864,848 12/1958 McArthur ..... 260/403 X
2,931,818 4/1960 McQuarrie ..... 260/403
3,577,446 5/1971 Rakhit ..... 260/403
4,159,988 7/1979 Eibl et al. ..... 260/403

OTHER PUBLICATIONS

Anjea, et al., Biochem. Biophys, Acta, 248, 455–457, (1971).

Sears, B., et al., Biochem. Biophys. Res. Comm. 60, 1141–1147, (1974).

Chandra, J., Chem. Phys. Lipids 4 104–108, (1970).

Dawson, R., Biochem J. 102, 76, (1967).

*Primary Examiner*—John F. Niebling
*Attorney, Agent, or Firm*—Richard P. Crowley

[57] ABSTRACT

Novel synthetic phosphatidyl ammonium hydroxide compounds are prepared which have a hydrophobic/-hydrophilic balance different from the natural phosphatidylcholine, which alterations are carried out by changes in the quaternary ammonium polar group to provide different surfactant properties.

8 Claims, No Drawings

PHOSPHATIDYL QUATERNARY AMMONIUM COMPOUNDS

Matter enclosed in heavy brackets [ ] appears in the original patent but forms no part of this reissue specification; matter printed in italics indicates the additions made by reissue.

BACKGROUND OF THE INVENTION

This invention relates to novel chemical compounds structurally related to phosphatidylcholine, to a method of preparing such compounds, and to the use as surfactants of such chemical compounds with or for compounds which have limited or no solubility in aqueous solutions.

Phospholipids and phosphatidylcholine in particular are amipathic compounds in that they consist of a hydrophobic and hydrophilic group or region within the same molecule. Compounds with this amipathic property tend to self-associate in aqueous systems to form micelles which have a hydrophobic interior and a hydrophilic exterior. As a result, these compounds act as surfactants and can solubilize other relatively aqueous insoluble compounds which have limited or no solubility in water, and can partition such insoluble compounds into the hydrophobic region of the micelle. The external polar hydrophilic region of the micelle confers water solubility on the micelle complex or group. It has been well known that such nonsoluble biological compounds, such as cholesterol, cholesterol esters and derivatives, triglycerides and other compounds, can be solubilized in phospholipid micelles. However, the extent of solubilizing power of any surfactant is highly dependent on the ratio of hydrophobic-to-hydrophilic balance within the particular molecule.

For example, natural phosphatidylcholine (that is, lecithin) is an excellent emulsifying agent for a number of insoluble biological compounds, such as cholesterol, cholesterol esters and triglycerides, and lecithin is widely used in many industrial applications; for example, the food industry. Lecithin is a natural surfactant, and, like other such surfactants, its solubilization properties are derived from its amipathic character; that is, the molecule possesses a region of hydrophobic character (the heterogeneous fatty-acid chain) and a region of hydrophilic character (the polar head group - ethyl-n-trimethyl group). In addition, lecithin is zwitterionic in the pH range of 2-12, because it possesses a positively charged group (the quarternary ammonium group) and a negatively charged group (the phosphate group). This zwitterionic character stabilizes the ionic structure of the lecithin against any pH fluctuations that would tend to flocculate other natural detergents; that is, other phospholipids or bile salts.

The natural occurring phospholipids are limited in solubilizing properties. For example, it is known that the maximum amount of cholesterol that phosphatidylcholine can solubilize is in a molar ratio of about one to one, while little, if any, cholesterol ester can be solubilized by phosphatidylcholine. Thus, novel phospholipid compounds which have modified solubilized properties (particularly those which solubilize a greater amount of both biological and industrial compounds than is possible with the natural compound or have different solubilized properties) would be most desirable and useful.

SUMMARY OF THE INVENTION

My invention relates to novel, synthetic, phosphatidyl ammonium compounds, particularly ammonium hydroxide compounds, which are characterized by enhanced or different solubilizing, surfactant and other properties from the heterogeneous, natural occuring phosphatidylcholine, to the method of preparing such compounds and to the method of using such compounds as surfactants to solubilize and emulsify other compounds, particularly cholesterol and cholesterol-derived compounds and triglyceride compounds.

I have discovered in particular that the solubilizing or surfactant properties of my novel phosphatidyl compounds can be obtained by variation in the separation of the positively and negatively changed groups; that is, by increasing or decreasing the distance between the groups, such as by increasing or decreasing the number of methylene groups between the charge moieties and/or by delocation of the positive charge on and about the quaternary nitrogen atom, such as by replacing one or more of the three methyl groups with other groups, such as with other alkyl groups. Thus, by taking advantage of the zwitterionic nature of natural phosphatidylcholine and changing the structure to produce novel compounds, modified and, in some cases, unexpected surfactant properties are obtained, particularly by the alteration and modification of the polar head group (the quaternary ammonium) and region of the various phosphatidylcholines.

My new compounds are useful and interesting substitutes for lecithin in solubilizing nonaqueous soluble compounds, and in particular such new compounds may be useful in the regression of atherosclerotic lesions and as antiatherosclerotic agents in blood or other biological fluids, and as stabilizing agents and emulsifiers, particularly in food products.

The novel synthetic phosphatidyl ammonium compounds of my invention are represented by the formula:

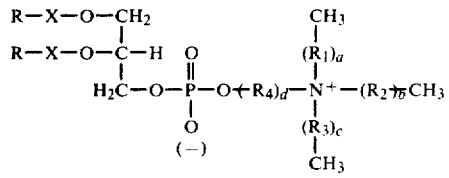

wherein X is a carbonyl group (C=O), R is a hydrocarbon radical, preferably a $C_{14}$ to $C_{20}$ fatty-acid radical; a, b, and c represent whole integers of from 0 to 3; d represents a whole integer of from 1 to 5, except that where a, b and c are zero (0) and d is two (2); and wherein $R_1$, $R_2$, $R_3$ and $R_4$ are hydrocarbon radicals, preferably methylene radicals, either straight or branch-chain radicals.

Some preferred phosphatidyl ammonium hydroxide compounds of my invention are represented by:

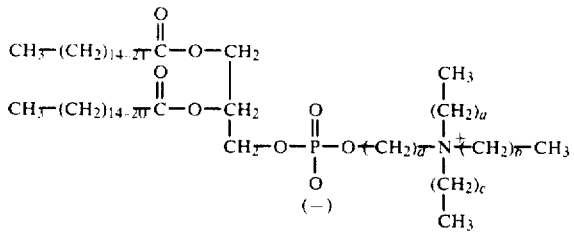

Typical compounds include:

| | | | |
|---|---|---|---|
| I: a = b = o | c = 1 | | d = 2 |
| II: a = b = c = o | | d = 4 | |
| III: a = b = c = o | | d = 3 | |
| IV: a = b = o | c = 2 | | d = 2 |

In my compounds, the R radicals may vary and be composed of natural or synthetic fatty radicals, but preferably are $C_{14}$ to $C_{20}$ fatty acid or alcohol radicals, or combinations and mixtures thereof. The fatty radicals useful include both saturated and ethylenically unsaturated hydrocarbon radicals such as those radicals derived from fatty acids or alcohols, such as, for example, myristate, palmitate, oleate, linoleate and stearate radicals and heterogeneous mixtures, such as found in natural products like egg yolk, soybeans and the like. The R and X radicals may be the same or different radicals, but preferably are the same X radicals with the same or different R radicals. In one method of preparation, as hereinafter described, the R radicals will be those radicals of the quaternary ammonium alcohol selected for the reaction. By the selection of desired fatty radicals and the length thereof, the hydrophobic character of this portion of the synthetic compound may be altered and modified to a desired defined length, such as by selecting the R radical to be the same or different chain length or degree of saturation or substitution.

The polar group or quaternary ammonium group of my compounds may be composed of substituent radicals to alter the electropositive character of the quaternary ammonium atom, but particularly are $C_1$–$C_4$ methylene radicals.

My novel compounds would include, but not be limited to:

dioleate phosphatidyl-(isopropyl-N-triethyl)ammonium hydroxide;

dipalmitate phosphatidyl-(ethyl-N-dimethyl, ethyl)ammonium hydroxide;

distearyl phosphatidyl-(ethyl-N-dimethylethyl)ammonium hydroxide;

oleate-palmitate phosphatidyl-(ethyl-N-dimethylethyl-)ammonium hydroxide;

dimyristate phosphatidyl-(butyl-N-dipropylmethyl)ammonium hydroxide;

dipalmitate phosphatidyl-(propyl-N-trimethyl)ammonium hydroxide;

egg phosphatidyl-(propyl-N-trimethyl)ammonium hydroxide;

soybean phosphatidyl-(propyl-N-trimethyl)ammonium hydroxide; and mixtures thereof.

My compounds have been described employing derived nomenclature. However, for example, dimyristate phosphatidyl-(butyl-N-dipropylmethyl)ammonium hydroxide above also may be named as dimystroyl phosphatidyl-(tetramethylene-N-dipropylmethyl) quaternary ammonium.

My compound may be prepared by a variety of methods. However, the preferred method of preparation is to prepare the synthetic phosphatidyl ammonium hydroxide by reacting and coupling the polar head group moiety to phosphatidic acid, for example, using triisopropylbenzenesulfonyl chloride in pyridine (see R. Anjea and J. S. Chandra, Biochem. Biophys. Acta 248, 455 (1971) and B. Sears, W. C. Hutton, and T. E. Thompson, Biochem. Biophys. Res. Comm. 60, 1141 (1974). The phosphatidic acid may be derived from natural or synthetic phosphatidylcholine by the digestion with the enzyme phospholipase D (see R. M. C. Dawson, Biochem J. 102, 76 (1967). The modified polar head group compound is then synthesized by the exhaustive alkylation of the derived corresponding hydroxylamine. The general reaction method is represented as follows:

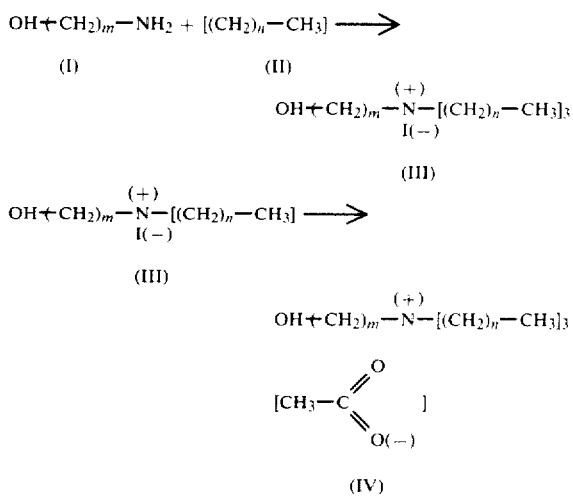

The salt form (for example, the acetate form) of the quaternary ammonium salt is obtained by ion-exchanging the quaternary ammonium halide salt (for example, the iodide form) in an ion-exchange column equilibrated with the acetate ions. Thus, my method is: to synthesize synthetic phosphatidylcholine or isolate natural phosphatidylcholine; then enzymatically to cleave the phosphatidylcholine to phosphatidic acid; to synthesize a modified quaternary alkyl ammonium hydroxide, convert the quaternary alkyl ammonium hydroxide to the corresponding acetate (the acetate form is more soluble than the hydroxide form in pyridine, the solvent used for coupling) and covalently couple with quaternary alkyl ammonium acetate onto the phosphatidic acid, thereby giving the phospholipid modified in the polar head group. The acetate or weak-acid form may also be used with acetonitrile as the solvent or the iodide form used where the coupling solvent is about a one:one mixture of pyridine and acetonitrile.

My methiod of preparing synthetic phosphatidyl quaternary ammonium compounds comprises covalently reacting or coupling in a common nonaqueous solvent typically an organic polar solvent like pyridine or acetonitrile; for example, a nitrogen-containing solvent, the quaternary ammonium salt preferably the weak acid salt or halo salt of the alkyl ammonium compound, with phosphatidic acid and recovering the phosphatidyl quaternary ammonium hydroxide compound and optionally chromatographically purifying the resulting compound.

My novel synthetic compounds have altered and modified hydrophobic-to-hydrophilic-balance properties over those of the natural compounds, as is demonstrated, for example, by variations in the migration rates of such compounds in thin-layer chromatography tests in comparison to the natural compounds. Such differences in the hydrophilic-to-hydrophobic balance will effect their surfactant properties.

My invention will be described for the purpose of explanation and illustration only in connection with the preparation of certain preferred compounds. However, it is recognized and is within the scope and intent of my invention and disclosure that other compounds and other methods of preparation can be formulated and used.

DESCRIPTION OF THE EMBODIMENTS

Synthesis of dipalmitoyl phosphatidyl ammonium hydroxide compounds

Glycerol phosphoryl choline was derived from crude egg yolk phosphatidylcholine using the method of J. S. Chandra, Chem. Phys. Lipids 4 104 (1970). Dipalmitoyl phosphatidylcholine was synthesized according to the method of Cubero Robles, E. and van de Berg, D., Biochem. Biophys. Acta 187 520 (1969). Dipalmitoyl phosphatidic acid was prepared by the enzymatic cleavage of dipalmitoyl phosphatidylcholine by cabbage phospholipase D according to Dawson, R. M. C., Biochem. J. 102 76 (1967). The appropriate hydroxy alkyl ammonium acetate was covalently linked to the dipalmitoyl phosphatidic acid using 2,4,6-triisopropylbenzenesulfonyl chloride as a coupling agent as described by Sears et al., Biochem. Biophys. Res. Comm. 60 1141 (1974). The phosphatidylcholine analog was then purified by silicic acid chromatography. The detailed synthetic description of the hydroxy alkyl ammonium compounds and the corresponding phosphatidylcholine compounds is described below.

A. Dipalmitoyl phosphatidyl-(ethyl-N dimethyl, ethyl) ammonium hydroxide (I).

0.975 g (10.9 millimoles) of dimethyl ethanolamine was placed in a 50-ml round-bottom flask. The flask was cooled to −10° C. and 1.159 g (7.43 millimoles) of ethyl iodine was added with stirring. The reaction mixture was allowed to warm slowly to room temperature and was then kept in the dark for 72 hours. At the end of 72 hours, the mixture was dissolved in 20 ml of 2 M $NH_4OH$. The solution was applied to a 2×40 cm column of Bio Rad 50W-X8 cation-exchange resin. The column was washed with 500 ml of 2 M $NH_4OH$. The (2-hydroxy ethyl)N-diemthyl, ethyl ammonium cation was released from the column by the addition of 300 ml of 0.5 M $NH_4HCO_3$. The (2-hydroxy ethyl)N-dimethyl-ethyl ammonium bicarbonate solution was evaporated to dryness and then taken up in distilled water. The solution was placed on a 2×40 cm column of Bio Rad AG1-X8 cation-exchange column in the acetate form. The column was eluted with distilled water. The (2-hydroxy ethyl)N-dimethyl-ethyl ammonium acetate was concentrated by dryness. Thin-layer chromatography in an isopropyl alcohol/water/14 M $NH_4OH$ (7:2:1) system gave only a single spot upon iodine staining. Colormetric analysis for quaternary ammonium salts gave an overall yield of 70% (7.7 millimoles). 375 micromoles of the (2-hydroxy ethyl)N-dimethyl-ethyl ammonium acetate in methanol was mixed with 275 micromoles of dipalmitoyl phosphatidic acid and then taken to dryness. The mixture was dried under high vacuum against $P_2O_5$ overnight. 760 micromoles of 2,4,6-triisopropylbenzenesulfonyl chloride in 5 ml of dry pyridine was added to the dry mixture. The reaction mixture was stoppered and heated and stirred for 1 hour at 65° C. and then stirred for 4 hours at room temperature. At the end of the reaction, the pyridine was evaporated from the reaction. The residue was taken up in 20 ml of chloroform-methanol (2:1) and then 5 ml of distilled water was added. The resulting lower phase was taken to dryness and the residue was taken up in chloroform. The chloroform solution was applied to 2×30 cm silicic acid column and the phosphatidylcholine eluted with increasing amount of methanol in chloroform. The phosphatidylcholine gave only a single spot by thin-layer chromatography. The yield based on colormetric phosphorus analysis was 17% (46.6 micromole). The elemental analysis gave the following results:

Theoretical: C: 64.31, H: 10.98, N: 1.83, P: 4.05;

Experimental: C: 64.12, H: 11.14, N: 1.66, P: 3.93

B. Dipalmitoyl phosphatidyl-(butyl-N-trimethyl)ammonium hydroxide (II).

1.0 g (11.2 millimole) of b 4-amino butanol was placed in a 50-ml flask and precooled to −10° C. 1.6 g (11.3 millimoles) of methyl iodine was added with stirring. The reaction mixture was allowed to warm to room temperature and was kept for 72 hours in the dark. The reaction mixture was purified as described for the (2-hydroxyl ethyl)-N dimethyl ethyl ammonium acetate. The final yield of (4-hydroxy butyl)-trimethyl ammonium acetate was 17% (1.8 millimoles). 750 micromoles of (4-hydroxy butyl)-trimethyl ammonium acetate and 500 micromoles of dipalmitoyl phosphatidic acid were mixed in methanol and taken to dryness. The mixture was dried under high vacuum against $P_2O_5$ overnight. 1250 micromoles of 2,4,6-triisopropylbenzenesulfonyl chloride in 10 ml of pyridine was added. The reaction was heated for 1 hour at 65° C. and then stirred for 4 hours at room temperature. The reaction was then purified as described above. The final yield of dipalmitoyl phosphatidyl-(butyl, N-trimethyl) ammonium hydroxide was 9.7% (48 micromoles) based on phosphorus analysis. Only a single spot was observed by thin-layer chromatography.

Elemental analysis:

Theoretical: C: 64.69, H: 11.0, N: 1.79, P: 3.98;

Experimental: C: 64.93, H: 10.72, N: 1.70, P: 4.12.

C. Dipalmitoyl phosphatidyl-(propyl-N-trimethyl) ammonium hydroxide (III).

2 g (26.6 millimoles) of 3-amino propanol was placed in a 50-ml round-bottom flask and cooled to −10° C. 3.78 g (26.6 millimoles) of methyl iodine was added with stirring. The stoppered reaction mixture was allowed to warm to room temperature. This flask was kept in the dark for 48 hours. The (3-hydroxy propyl)-trimethyl ammonium salt was purified and converted to the acetate salt as previously described. Only a single spot was seen by thin-layer chromatography. The yield by colormetric analysis was 21% (5.5 millimoles). 367 micromoles of (3-hydroxy propyl)-trimethyl ammonium acetate and 245 micromoles of dipalmitoyl phosphatidic acid were mixed in methanol and evaporated to dryness. The residue was dried at high vacuum and against $P_2O_5$ for 12 hours. 612 micromoles of 2,4,6 triisopropylbenzenesulfonyl chloride in 5 ml of pyridine was added. The reaction was heated at 65° C. for 1 hour and then stirred for 4 hours at room temperature. The dipalmitoyl phosphatidyl(propyl-N-trimethyl ammonium hydroxide was purified as previously described. Only a single spot was seen by thin-layer chromatography.

The elemental analysis was as follows:

Theoretical: C: 64.48, H: 10.92, N: 1.70, P: 3.88;

Experimental: C: 64.31, H: 10.98, N: 1.83, P: 4.05.

D. Dipalmitoyl phosphatidyl-(ethyl-N-dimethyl, propyl)ammonium hydroxide (IV).

0.975 g (10.9 millimoles) of dimethyl ethanolamine was placed in a 50-ml round-bottom flask and cooled to −10° C. 5.61 g (33 millimoles) of propyl iodine was added with stirring. The mixture was allowed to warm to room temperature and was then kept in the dark for 72 hours. The (2-hydroxy) N-dimethyl, propyl ammonium acetate was purified as previously described. 750 micromoles of (2-hydroxy)-N-dimethyl, propyl ammonium acetate and 500 micromoles of dipalmitoyl phosphatidic acid were acid in methanol and taken to dryness. The residue was dried under high vacuum and against $P_2O_5$ overnight. 1250 micromoles of 2,4,6 triisopropylbenzenesulfonyl chloride in 15 ml of pyridine was added to the residue. The mixture was heated for 1 hour at 65° C. and then stirred for 4 hours at room temperature. The purification of the dipalmitoyl phosphatidyl-(ethyl-N-dimethyl, propyl) ammonium hydroxide was carried out as previously described. Thin-layer chromatography showed only a single spot.

The elemental analysis gave the following:

Theoretical: C: 64.69, H: 11.00, N: 1.79, P: 3.98;

Experimental: C: 65.16, H: 11.74, N: 1.78, P: 3.96.

I have described the synthesis of a selected number of preferred phosphatidylcholine compounds in which the hydrophilic region of the molecule has been chemically modified. As a result, the hydrophobic-to-hydrophilic balance within the molecule is altered. One criterion of this alteration is the relative mobility of these new compounds on silicic-acid, thin-layer chromatograms. The mobility of the compound is directly related to the molecular structure of the molecule.

By changing the hydrophilic region of the phosphatidylcholine molecule, all of the described compounds now have different migration rates. Three of the compounds (A, B, D) have mobilities greater than the phosphatidyl, whereas one (C) has a mobility less than phophatidylcholine. Therefore, the hydrophobic-to-hydrophilic balance in each of the phosphatidylcholine molecules has been altered. These new compounds have utility as solubilizing agents in food-processing, industrial and biological applications. In addition, because of their close structural relation to phosphatidylcholine, they also find application in clinical medicine, such as the regression of atherosclerotic lesions, via the solubilization of deposited cholesterol.

What I claim is:

1. A synthetic phosphatidyl quaternary ammonium compound represented by the formula:

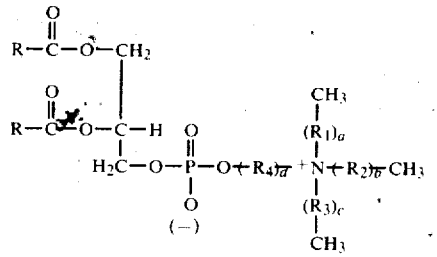

wherein R is a $C_{14}$ to $C_{20}$ hydrocarbon radical; a, b and c represent whole integers of from 0 to [3] *2 and a, b and c in total are equal to at least one*; d represents *a* whole [integers] *integer* of [from 1 to 5, except that in combination a, b and c cannot be zero and d cannot be two] *2*; and $R_1$, $R_2$, $R_3$ and $R_4$ are methylene radicals.

2. The compound of claim 1 wherein R is an ethylenically unsaturated hydrocarbon radical.

3. The compound of claim 1 wherein R is a fatty radical.

4. The compound of claim 1 wherein the R radicals are different hydrocarbon radicals.

5. The compound of claim 1 wherein a, b and c [are zero] *in total are equal to one.*

[6. The compound of claim 1 wherein $R_4$ is a tetramethylene radical and a, b and c are zero.]

[7. The compound of claim 1 wherein $R_4$ is a trimethylene radical and a, b and c are one, and $R_1$, $R_2$ and $R_3$ are a methylene radical.]

[8. The compound of claim 6 wherein R is a fatty radical.]

9. The compound of claim 1 wherein

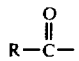

is a myristoyl, palmitoyl, oleoyl, linoleoyl, stearoyl, egg yolk or soybean radical.

10. The compound of claim 1 selected from the group consisting of:

[dioleoyl phosphatidyl-(methylethylene-N-triethyl-)ammonium;]

dipalmitoyl phosphatidyl-(ethylene-N-dimethylethyl-)ammonium;

distearoyl phosphatidyl-(ethylene-N-dimethylethyl-)ammonium; *and* oleoyl-palmitoyl phosphatidyl-(ethylene-N-dimethylethyl)ammonium[;

dimyristoyl phosphatidyl-(tetramethylene-N-dipropylmethyl)ammonium;

dipalmitoyl phosphatidyl-(trimethylene-N-trimethyl-)ammonium;

egg phosphatidyl-(trimethylene-N-trimethyl)ammonium;

soybean phosphatidyl-(trimethylene-N-trimethyl-)amonium; and dipalmitoyl phosphatidyl-(tetramethylene-N-trimethylene)ammonium].

[11. The compound of claim 6 wherein

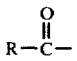

is a myristoyl, palmitoyl, oleoyl, linoleoyl, stearoyl, egg yolk or soybean radical.]

*12. The compound of claim 1 wherein $R_1$, $R_2$ and $R_3$ are not the same number of methylene radicals.*

* * * * *